United States Patent [19]

Rudat et al.

[11] Patent Number: 5,256,547

[45] Date of Patent: Oct. 26, 1993

[54] PROCESS FOR MAKING AND ISOLATING CYCLOSPORIN A BY FERMENTATION

[75] Inventors: Wolf-Ruediger Rudat, Dresden; Ernst-Joachim Bormann, Jena; Guenter Arnold, Weimar, all of Fed. Rep. of Germany

[73] Assignee: Arzneimittel Dresden GmbH, Radebeul, Fed. Rep. of Germany

[21] Appl. No.: 689,157

[22] Filed: Apr. 22, 1991

[51] Int. Cl.$^5$ .................. C12P 21/00; C12P 21/04; C12R 1/645

[52] U.S. Cl. ............... 435/71.1; 435/71.3; 435/803; 435/911; 435/171; 435/254.1; 530/317; 530/321

[58] Field of Search ............ 435/71.1, 71.3, 171, 435/254, 803, 911; 530/317, 321

[56] References Cited

U.S. PATENT DOCUMENTS

| | | | |
|---|---|---|---|
| 4,117,118 | 9/1978 | Harri et al. | 530/321 |
| 4,215,199 | 7/1980 | Harri et al. | 435/71.1 |
| 4,288,431 | 9/1981 | Traber et al. | 435/71.1 |
| 4,289,851 | 9/1981 | Traber et al. | 435/71.1 |

Primary Examiner—Herbert J. Lilling
Attorney, Agent, or Firm—Michael J. Striker

[57] ABSTRACT

Method of fermentative production and isolation of Cyclosporin A by aerobic fermentation of a fungus microorganism in a medium containing mineral salts, a nitrogen-containing substrate, including using a producer strain consisting of strain Wb 6-5 of *Tolypocladium inflatum*, IMET 43 899 *Sesquicilliopsis rosariensis* G.ARNOLD, IMET 43 888, *Sesquicilliopsis rosariensis* G.ARNOLD F605, IMET 43 887, a mutant thereof or a strain obtained therefrom by selection; culturing the producer strain in a culture medium containing an ammonium salt as a single source of nitrogen; mixing the culture medium with a filter aid to form a suspension; after the mixing step, filtering the suspension to form a filter cake containing moist biomass and filter aid; drying the filter cake after the filtering; after the drying step, extracting the filter cake with a supercritical gas, advantageously carbon dioxide, or a lower carboxylic acid ester to form an extract; distributing the extract between aqueous methanol solution and petroleum ether to remove fats and form a purified extract; and chromatographing the purified extract by preparative HPLC using silica gel or aluminum oxide.

16 Claims, No Drawings

PROCESS FOR MAKING AND ISOLATING CYCLOSPORIN A BY FERMENTATION

BACKGROUND OF THE INVENTION

The present invention relates to a process for making the cyclic oligopeptide, cyclosporin A, and, more particularly, to a microbiological method using a new producer strain to make and isolate cyclosporin A.

Cyclosporin A is a member of a group of cyclic undecapeptides with antiinflammatory, immunosuppressive, antifungal and antiparasitic properties. The immunomodulatory properties are of particular interest in medicine, since they are important in treatments of transplantation surgery and for autoimmune diseases.

Cyclosporins are a new class of compounds, which were first described in Swiss Patent 589,716 and 603,790. They have also been reviewed in the Monograph by Borel (Cyclosporin, Progress in Allergy 38, Karger Press, 1986). The chemical structure and biological-pharmacological properties were described in the latter Monograph.

In the production method for Cyclosporin A, the ability of microorganisms for synthesis of the naturally occurring Cyclosporins is used, since one cultivates certain species of microorganisms as producing agents in a fermentation process using the standard culturing conditions in a nutrient solution, which contains a complex substrate. Similarly in a way, which is generally known, one isolates the desired product and purifies it.

In extensive screening experiments numerous fungus species were found to have cyclosporin-forming properties. DREYFUSS (Sydowia, Bd. 39, 1986, pp. 22 to 36) describes an exclusively emersed Cyclosporin-forming capability for Cylindrocarpon and Fusarium fungi, while Cyclosporin formation was detected in submersed cultures of Hyphae fungi, *Tolypocladium geodes, Trichoderma viride, Neocosmospora vasinfecta, Isaria felina Verticillium spec., Acremonium spec.* and *Beauveria nivea* (originally *Tolypocladium inflatum*). The highest productivity can be obtained with strains of the fungi, *Beauveria nivea*. This strain is of particularly significance for the large scale production of Cyclosporin A. According to the description by TRABER et al (in J.Antibiotics, Vol. 42, 1989, pp. 591 to 597) a mutant of *Beauveria nivea* (in the cited article described as a mutant of *Tolypocladium inflatum* NRRL 8044) produces about 500 mg of Cyclosporin A per liter. In a chemical synthetic medium containing malic acid and sucrose and ammonium as nitrogen source KOBEL and TRABER (Europ. J. Appl. Microbiol.Biotechnol., vol. 14, 1982, pp.237-240) obtain a yield of 101 mg Cyclosporin A per liter in 14 culture days. By feeding with select aminoacids in a concentration of 8 g/l, the yield level could be improved, but this method is however in no way relevant for an economic industrial production method. Similar disadvantages are present in the fermentation method of AGATHOS et al (Ann.N.Y. Acad.Sci. 506, 1987, pp. 657-662), which describes a fermentation in a semisynthetic medium with a yield of 530 mg cyclosporin A per liter after 16 culture days. However, in this method the use of maltose leads to a high rate of operating expense in an industrial process.

Regarding the economics of using a producing strain, the described volume-time-yields for an industrial process are exceptionally unsatisfactory, which causes other disadvantages in the isolation and purification of different cyclosporins, particularly cyclosporin A, connected necessarily with loss of agent. The described methods for isolation of Cyclosporin A from a culture suspension of different strains must consider in all cases the expected sensitivity of the peptide bond in the Cyclosporin-A molecule and begins by avoiding higher temperatures with a liquid-liquid extraction of the culture suspension or with an extraction of the separated wet mycelium (U.S. Pat. No. 4,117,118; U.S. Pat. No. 4,215,199; German Patent 2 455 859; Belgian Patent 866 810; v. Wartburg et al, Helv.Chim.Acta 59,(1976), p. 1075). The extraction residue is usually distributed between 30% methanol and petroleum ether and the material with fat removed is repeatedly chromatographed on silica gel, aluminum oxide and/or Sephadex LH 20, on which a considerable adsorption occur, which proceeds up to 1000-fold of the substrate(German Patent 2 455 859). This extensive purification work and the stress of immediate work-up of the producing culture media with wet mycelium are substantial difficulties for the known production methods. Of particular disadvantage in the known methods is the high cost of the solvents used, particularly because they are not environmentally friendly. Also environmental considerations must come into play in their disposal.

SUMMARY OF THE INVENTION

It is an object of the present invention to increase the number of available highly productive Cyclosporin-forming strain.

It is also an object of the present invention to provide an economical efficient microbiological process, which utilizes newly produced microorganisms to manufacture Cyclosporin A in a synthetic media without the use of complex nitrogen-containing substrates.

It is yet another object of the present invention to provide an industrially advantageous, environmentally friendly and efficient method of isolating and purifying Cyclosporin A with a good yield.

It is an additional object of the present invention to provide an environmentally friendly and efficient method of isolating and purifying Cyclosporin A with a good yield, in which a minimum of auxiliary materials are used and in which the auxiliary materials are non-polluting.

In harmony with the objects of the present invention a new, currently unknown microorganism was isolated from a natural habitat in the subtropic climate zone. This new microorganism was cultured purely and it not only produced the desired materials which act as metabolites, but it produced the desired products, especially Cyclosporin A, in unexpectedly large quantities depending on the strain conditioning as a result of mutagenic and selection processes under submersed culture conditions in a multistep industrial fermentation process. This result is particularly surprising, since known completely synthetic chemical media were up to now regarded as not suitable for synthesis of a producing culture on this large scale.

The original microorganisms, which were members of the imperfect hyphae fungi, were isolated using a ground probe from the Sierra del Rosario (Cuba) and are taxonumerically a new genera and species, *Sesquiciliopsis rosariensis* G.ARNOLD.

These original organisms were grown in different nutrient media, which contain the usual nutrient substances for fungi. In culturing on Malz-Agar with natural day-night-rhythms an approximately 8 cm colony is formed after about 10 days, with a weakly formed, light, flaky, white air mycelium, which extended up to the colony edge. A ring formation is observed only weakly in the outer portion of the colony. A weak odor with a soup flavor is formed. The air mycelium comprises a septated, branched hyphae, which appears in the mass white. The ascending hyphae are usually strong and more or less whorled or irregularly branched, carrying on their many branches several phialide arising by overculmination, which are formed colorless, awl-like and slender. The conidiums are formed several in succession on the peaks of the phialide. They are elongate, one cellular, hyalin, smooth-walled and thin-walled, adhering to a small head. Chlamydospores were not observed.

The strain, *Sesquicilliopsis rosariensis* G.ARNOLD. is different from similar types with phialidic, conidiophore cells (e.g. microconidium-forming Fusarien, Gliocladium. Verticillium, Sesquicillium, Sympodiophora), because of certain special features, above all because of the type and orientation of the conidiophore cells.

The new microorganism *Sesquicilliopsis rosariensis* G.ARNOLD A84/195-(3), which is used in the present method for making Cyclosporin A, was deposited Aug. 8, 1988 according to the Budapest Treaty at the IMET-Culture Collection at Beutenbergstrasse 11, D-6900 Jena, Federal Republic of Germany under accession number IMET 43888. Similarly, the high yielding strain *Sesquicilliopsis rosariensis* G.ARNOLD A84/195-(3) mutant F 605 was deposited on Aug. 8, 1988 according to the Budapest Treaty at the IMET-Culture Collection at Beutenbergstrasse 11, D-6900 Jena, Federal Republic of Germany under accession number IMET 43887. The invention naturally includes using all variants obtained by mutation and/or selection of the original naturally occurring wild strains or variants grown from the above-mentioned mutants.

The strain variant Wb 6-5 of *Tolypocladium inflatum* could be isolated by selection of high-yielding monospore lines in certain chemical nutrient media, particularly containing zinc ions.

The isolation of this strain variant is particularly surprising based on the view present in the Literature, that large-scale cyclosporin-formation can only occur in the presence of complex nutrient substances, such as peptone or certain amino acids, which an economic process permits. The selectant Wb 6-5 of the strain *Tolypocladium inflatum* was deposited on Nov. 28, 1988 according to the Budapest Treaty at the IMET-Culture Collection at Beutenbergstrasse 11, D-6900 Jena, Federal Republic of Germany under accession number IMET 43899.

According to the method for making Cyclosporin A according to the invention, the selectant Wb 6-5 of *Tolypocladium inflatum* or the strain variant F605 of *Sesquicilliopsis rosariensis* G.ARNOLD is cultured in a medium with ammonium salt as a single available nitrogen source and, if necessary, also with citrate and in the presence of selected divalent cations. Moreover it has proven advantageous, when one proceeds with the fermentation of individual strains from red-brown to blackish-brown-violet pigmented emerse culture portions, which are grown in mineral salt-glucose-agar with ammonium salts, since this guarantees a stable Cyclosporin A production. Further, it is particularly beneficial, to use ammonium sulfate and/or diammonium hydrogen phosphate as an inorganic nitrogen containing compounds in the production culture media. The zinc ion concentration for culturing this strain should advantageously be selected in the range from 0.5 mg/l to 5.0 mg/l. It is remarkable that the productivity of the Selectant Wb 6-5 is negatively influenced in a surprising way by the presence of calcium salts and/or calcium ions. This fact is surprising, because all media published for this strain include the calcium ion or calcium salt. This kind of dependence could not be established for Strain F605 of the *Sesquicilliopsis rosariensis* G.ARNOLD. For the latter strain the presence of certain divalent metal ions in the fermentation media is of importance, especially the availability of magnesium, iron, zinc and calcium ions, which exert a direct influence, but also to a different extent, on the synthetic activity. Thus the fermentation of strain F605 should be performed advantageously with a magnesium concentration of 250 mg/l, an iron concentration of 20 mg/l and a zinc concentration of 0.7 mg/l. It is especially important to pay attention to supplying a measured amount of calcium ion such that the calcium ion concentration lies between 10 mg/l and 200 mg/l, since in the absence of calcium the strain F605 is not productive. Simultaneously, it has proven advantageous for this strain variant, to perform the culturing in the presence of citrate ions in the range of from 5 g/l to 30 g/l, advantageously at 12 g/l.

Despite the different needs of the individual Cyclosporin A-producing strain in regard to the content of certain divalent cations in the production medium for all strains in the present method the decisive progress consists in elimination of a costly nitrogen source which is heterogeneous in its composition. This result was unexpected, in as much as ammonium and nitrate were described as unsuitable in regard to Cyclosporin production in AGATHOS et al,, J.Ind.Microbiol., Vol. 1, 1986, pp. 39 to 48). These authors recommend a complex nitrogen source as the sole nitrogen-containing substrate. Also the later published result with inorganic N-source (MARGARITIES and CHAHA, Biotechnol. Lett., Vol 11, 1989, pp. 765–768) make the same abovementioned assertion.

The fermentation occurs after a one and/or two-step pre-cultivation in a submersed main culture under aerobic and sterile conditions, cultivating the different producing strains in a fluid media at temperatures from 20° to 30° C. and an acidity of 3.0 to 7.5 for 5 to 11 days.

The course of this entire process has the following general characteristics:

Mycelium pieces from the emerse culture of strain Wb 6-5, and/or also their spores, are suspended in 0.9% NaCl and spread on a solid medium, which contains mono- or disaccliarides and ammonium sulfate as a nitrogen-containing source, are cultivated for 14 to 21 days at 24° to 28° C., advantageously at 24° C. The culturing of Strain F605 occurs in the same way, however without ammonium sulfate in the nutrient agar. From the arising individual colonies, the air mycelium-poor, red- to black-brown pigmented portions are selected and used after transfer to a mineral salt-carbohydrate-agar to make mycelium areas which are from 2 to 4 cm ion size. These are transferred, as choice starting materials, (a piece of mycelium with agar) to a first submersed pre-culture, which is cultured in a 100 ml and/or 500 ml Erlenmeyer flask, which contains about 20% of its volume as culture medium. The nutrient solution contains glucose, maltose or sucrose as carbohydrate source, and also organic or inorganic nitrogen substrates and mineral salts and is cultured in a rotatary shaking device at 100 to 240 rpm after inoculation for a duration of 48 to 96 hours at 24° to 28° C. After maturation of the first culture in the liquid phase (corresponding to the first pre-culture), an inoculation of a second culture (corresponding to a second pre-culture occurs as needed) with an inoculation of 5 to 10% of the volume of the nutrient solution of the subsequent culture. This step occurs either in a 500 ml erlenmeyer flask, which contains 100 ml of the culture media, or in a plurality of small fermentation vessels which are stirred and aerated and have a net volume of 5 to 25 l with the standard conditions for tempering and aeration. After 48 to 96 hours cultivation, the main culture media, which contains ammonium salts as the sole nitrogen source, is inoculated with an amount of from 5 to 10% of volume with the preculturing product and is stirred and aerated from 5 to 20 days or cultivated by a rotary shaking device. Under these conditions the fermentation production is determined to be up to 3000 mg Cyclosporin A per liter, which was measured by HPLC in a known way. At the time for harvesting, the culture suspension has a red- to blackbrown color.

The isolation of Cyclosporin A from the culture suspension in the method of the invention comprises mixing this culture suspension with a filter aid, subsequently filtering the culture suspension with the filter aid, drying the moist biomass and filter aid, extracting a product mixture from the biomass and filter aid with a lower carboxylic acid ester, or alternatively with a supercritical gas, advantageously carbon dioxide, and extracting the product mixture by distribution between a water-containing methanol solution and a petroleum ether to removing fat and grease from the product mixture to form a purified extract and subsequently chromatographing the purified extract on silica gel and/or aluminum oxide.

The advantages of this method of isolation are as follows:
separation of the biomass without losses despite the small particle size, formation of a driable material, which is extractable, stable and storable;
extraction process with reduced portions of ballast material with reduced cleaning expense;
adaption of the additional cleaning steps to the special properties of the products; and
reduced use of extraction material.

It has proven to be difficult that the biomass of the products does not come down as preferred in hyphae form, but instead in corpuscular form with a particle size of from 10 to 30 micrometers and forms a poorly filterable, difficult-to-separate filter cake. According to the invention, these difficulties are surmounted, since the culture suspension is mixed directly or after preliminary concentration by centrifugation with a filter aid of sufficient separating power (e.g. recrystallized gypsum, advantageously either Precosite or calcite meal) and subsequently filtered. A mass ratio of filter aid/biomass of from 1:1 to 4:1 guarantees a good filterability, rapid drying and effective residue separation after extraction. The moist biomass, which contains between 35 and 60 % by mass, surprisingly, inspite of its peptide nature, allows conversion into a stable dry mycelium preparation practically without substance loss by convective drying (e.g. vacuum drying chamber, circulating air drying chamber, whirling stream and band dryer) at temperatures up to 80° C., advantageously 40° to 60° C. The ratio of moisture to dry solid in this product is from 0.02:1 to 0.15:1. An alternative consists in Lyophilization, which provides a stable and extractable dry product.

The following twice or three times repeated extraction advantageously occurs with acetic acid ester, since less ballast material accompanies it than, for example, with ethanol or acetone. This is particularly true, when there are only two extractions. The residue remaining after evaporation is distributed between a water-containing methanol solution or ethanol solution and petroleum ether and contains already a substance composition of about 40% by mass. Moistening the mycelium prior to extraction with ammoniacal water can be considered appropriate. On processing difficult to extract mycelium varieties, the mycelium is swollen prior to extraction with 20 to 40% mass, advantageously 25% mass, after 8 to 72 hours and the first extraction is performed with an Ultra-Turrax.

Alternatively for a solid-fluid extraction with organic solvent the material can also be extracted with a supercritical gas, particularly carbon dioxide, from which dry mycelium is extracted. Pressure and temperature depend on which gas is chosen. For carbon dioxide a meaningful effective range is from about 100 to 300 bar and 35° to 60° C. Appropriately, the Extraction is aided by addition of an activator, e.g. 0.5 to 1.5% by mass ethanol to the carbon dioxide. Impurities, above all fats, can be separated by multistep extraction and/or fractionation separation.

The first column chromatography purification occurs either using neutral aluminum oxide (500 to 100-fold amounts) or silica gel (30 to 60 fold amounts) with acetic acid ethyl ester as mobile phase. The second purification occurs always with silica gel, advantageously with 40-fold amounts in ethyl acetate. In a reasonable further development of the supercritical extraction additional material selection by HPLC is possible alternatively to normal pressure-liquid chromotography.

The invention, as defined in the claims appended below, is not to be construed as being limited by the details of the Examples presented below, which are presented as preferred embodiments of the method of our invention.

EXAMPLES

Example 1

Mycelia pieces from surface cultures of the strain, *Tolypocladium inflatum* Wb 6-5, are transferred first to glucose-mineral salt Agar, which has the following composition (g/l): Glucose 20; $(NH_4)_2SO_4$ 5; $KH_2PO_4$ 2; $MgSO_4 \cdot 7H_2O$ 0.5; $CaCO_3$ 3.4; Agar 20; and a pH-value 5.3 to 5.7, which was sterilized for 30 minutes at 120° C. After incubation of the Petri dish containing the culture at 24° C. for 14 to 21 days, the red and blackbrown pigmented areas present were selected. The inoculation of the first submersed pre-culture occurs by transfer of about 1 $cm^2$ of the mycelia pieces from the culture plate to 100 ml of a liquid culture medium of the following composition (g/l): glucose 50; casein peptone 10; $KH_2PO_4$ 1; KCl 2.5; ad 1 l of distilled water; and a pH value of 5.3 to 5.6. This medium was sterilized for 30 minutes at 120° C. The inoculated liquid culture medium was cultured in a 500 ml culture flask for 72 hours at 24 to 25° C. with 180 to 220 rpm in a rotary shaking device. The end of the culturing process is indicated by a brownblack color. 5% portions of the product of the above culturing are used to inoculate 100 ml portions of the main liquid culture medium each in a 500 ml Erlenmeyer flask. This liquid culture media has the following composition (g/l): Glucose 80; $NH_{42}SO_4$ 5; $(NH_4)_2HPO_4$ 2; $MgSO_4*7H_2O$ 0.5; $ZnSO_4*7H_2O$ 0.008; $CaCO_3$ 5.1; in distilled water ad 1 l; and at pH 5.3 to 5.9. Sterilization of this main culture media occurs for 30 minutes at 120° C. The cultivation occurs for 11 days at 24° to 25° C. in a rotary shaking device at 180 rpm.

At the end of the fermentation process the culture broth is mixed with methanol 5:1 and the extract is evaluated. This occurs in a way known in itself by loading an HPLC column. The yield of the fermentation amounts to 1100 mg Cyclosporin A per liter.

Example 2

A spore suspension, which is used to inoculate a pre-culture, is made after at least 14-days cooking at 24° C. from an emersed culture of the strain, *Sesquicilliopsis rosariensis* G.ARNOLD F605, in a Malt extract (20 g malt extract/l). The pre-culture has the following composition (g/l): maltose or glucose 75; Casein peptone 25; $KH_2PO_4$ 1; KCl 2.5; deionized water 1 l; and pH value 5.5. Sterilization occurs for 30 minutes at 120° C. 100 ml of pre-culture medium are inoculated with $2*10^7$ spores and cultivated at 24° C. for 72 hours in a 500 ml Erlenmeyer flask on a rotary shaking device at a frequency of 190 rpm. Subsequently, the transfer of the culture into a main liquid culture media occurs with a ratio of 1:10, the main culture liquid having the following composition (g/l): glucose 100; diammoniumhydrogen citrate 15; $KH_2PO_4$ 1; $MgSO_4*H_2O$ 2.5; $FeSO_4*7H_2O$ 0.1; $ZnSO_4*7H_2O$ 0.003; deionized water ad 1 l; pH value 5.5. The medium is first sterilized at 110° C. for 60 minutes. All culture conditions are chosen according to the pre-culture. The content of Cyclosporin A after 11 culture days amounted to a maximum of 1150 mg/l culture suspension. The analysis of the material occurs as described in example 1.

Example 3

Growth and culturing of strain F605 occurs in the pre-culture as in Example 2, however in contrast the producing strain after the pre-culture is transferred into a 5 l fermentor, which already contains the main liquid culture medium described in Example 2 and is aerated with a volume flow of from 0.25 to $1.0 \, l*min^{-1}l^{-1}$ and stirred at 200 to 500 $min^{-1}$. The fermentation proceeded for 14 days and results in Cyclosporin A yield of a maximum of 3150 mg/l.

Example 4

After an inoculation material culturing of strain F605 performed according to example 2, a stirred fermenting vessel containing the following nutrient solution (g/l): glucose 50; soya coarse meal 2.5; $(NH_4)_2SO_4$ 4.1; $KH_2PO_4$ 5.0; pH value 5.5. is inoculated with $2*10^8$ spores per liter. Temperature, stirring and aerating correspond to the conditions described in Example 3 for the main liquid culture media. The culture obtained in four days serves as a 10 % inoculate for the production step in a 450 l fermentor made from alloy steel, which contains the main liquid culture medium described in Example 2 and is cultivated using the above described culturing conditions.

In the fermentation, which was performed in the previously described manner, after 14 culture days 2 grams of Cyclosporin A per liter of culture suspension were formed.

Example 5

6 l of culture suspension of the strain F605 of the species, *Sesquicilliopsis rosariensis* G.ARNOLD F605 IMET or the strain Wb 6-5 of species Tolypocladium inflatum(IMET 42899), 43 887), are separated by a manual filter plate covered with Precosite, and the moist product is dried in a circulating air drying chamber for 6 hours at 50° C. One obtains 246 g dry mycelia-Precosite mixture, which contains about 50% by mass Precosite. The mixture is preswelled with 60 ml 10% aqueous ammonia for 15 minutes and is stirred in three portions for three times with 4.2 l acetic acid ethyl ester for thirty minutes each. The entire extract was filtered to remove solids. 21 g of residue were left after distillation of the solvent. This 21 g of residue was received in 100 ml of ethanol, which contained 5% water; it was shaken three times with three successive portions 300 ml each of petroleum ether. Evaporation of the ethanol reduced this to 14 g.

The column chromatographic purification on 1000 g aluminum oxide neutral, active state I, in acetic acid ethyl ester supplies, after about 500 ml of preliminary eluent, a 1450 ml main fraction. After rechromatography of the residue on silica gel 60 Merck (0.063 to 0.2 mm) in the same solution and agitation with a 7-fold amount of n-Hexane, one obtains 5.2 g of almost white product with 99% by mass Cyclosporin A according at HPLC analysis.

Example 6

A volume of 327.5 l of culture suspension of the mutants named in Example 5 with a portion of 21.2% dry biomass are mixed with 13.1 kg Precosite and filtered in two portions in a pressure filter with a filter surface of 0.5 $m^2$ (centrifugal disk filter, Seitz type). The filter surfaces were covered with a Precosite-base deposit of 250 g per charge. The moist filter cake (mass 28.5 kg) is dried in a fluidized bed drier at an air temperature of from 35° to 55° C., so that a dry mycelia-Precosite mixture arises with a mass of 15.4 kg. The dry mass is stirred in a stirred suction filter first with 100 l, then with 70 l acetic acid ethyl ester each 30 minutes. The clarified and purified extract is concentrated first in a vacuum-rotary evaporator, then in a vacuum rotating evaporator until at the above-named residue, which is taken up in 8 l of methanol. After addition of 0.4 l water, the result is stirred with 16 l petroleum ether. The separated methanol phases yield 600 g of residue after concentration in a vacuum rotary evaporator. The first column chromatographic purification in 24 kg of silica gel 60 Merck in acetic acid ethyl ester provides 275 g of a 79 percent raw cyclosporin material. The rechromatography occurs on 14 kg silica gel 60 Merck in methylene chloride with 2.5% by weight methanol component. Yield: 102 g, content (HPLC) 97.5% Cyclosporin A.

Example 7

A vacuum rotary cell filter with 0.3 $m^2$ filter surface is coated with 10 kg Precosite as primary deposit. One filters 290 l of a culture suspension of the mutants described in Example 5 with it. The culture suspensions are mixed prior to filtration with 60 g/l Precosite. One obtains 62.5 kg for moist filter cake with 55.4% water content. 50 kg of this moist mass are dried in a fluidized bed drier and provide 22.5 kg dry mycelia-Precosite mixture with an active ingredient of 6.3 g/kg of mixture.

Example 8

20 kg of the dry mycelia-Precosite mixture obtained according to Example 7 are wet with 5 l of Methanol and stand in a closed container for 24 hours at room temperature.

After that, one transfers the material into 50 l ethyl acetate and centrifuges with Ultra-Turrax for 40 minutes. After vacuum filtration the filtrate is stirred with an additional 50 l of ethyl acetate for 10 minutes and subject to vacuum filtration. The residue of the combined extracts is processed in a manner similar to Example 6 and contains about 61.5 g of pure Cyclosporin A.

Example 9

0.52 kg of the dry mycelia-Precosite mixture (TMP) obtained in Example 7 are extracted with 5.2 to 6.5 kg/hr supercritical carbon dioxide at 300 bar and 40° C. with addition of 50 to 80 ml ethanol over at time period of about 6 hours. About 60% of the TMP extracted contains Cyclosporin A. The extract so obtained is further processed analogously to Example 6 to obtain the pure Cyclosporin A.

While the invention has been illustrated and described as embodied in a process for making and isolating Cyclosporin A by fermentation and a new Cyclosporin-forming Strain, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. Method of fermentative production and isolation of Cyclosporin A by aerobic fermentation of a fungus microorganism in a medium containing a salt and a nitrogen-containing substrate, comprising the steps of:
   a. using a producer strain selected from the group consisting of Wb 6-5 of *Tolypocladium inflatum*, IMET 43 899, *Sesquicilliopsis rosariensis* G.ARNOLD, IMET 43 888, *Sesquicilliopsis rosariensis* G.ARNOLD F 605, IMET 43 887, mutants thereof and strains obtained therefrom by selection;
   b. culturing said producer strain in a culture medium containing an ammonium salt as a single source of nitrogen;
   c. after the culturing step b), mixing the culture medium with a filter aid to form a suspension;
   d. after said mixing step c), filtering the suspension to form a filter cake containing moist biomass and filter aid;
   e. drying the filter cake after the filtering;
   f. after the drying step e), extracting the filter cake with an extraction means to form an extract;
   g. distributing the extract between aqueous methanol solution and petroleum ether to remove fats and form a purified extract; and
   h. chromatographing the purified extract by preparative HPLC using a member selected from the group consisting of silica gel and aluminum oxide to obtain the cyclosporin A.

2. The method according to claim 1, wherein the extraction means comprises a carboxylic acid ester.

3. The method according to claim 2, wherein the carboxylic acid ester comprises ethyl acetate.

4. The method according to claim 1, wherein the extraction means comprises supercritical gas.

5. The method according to claim 4, wherein the supercritical gas comprises supercritical carbon dioxide.

6. The method according to claim 1, wherein the culture medium also contains a divalent cation and citrate anion.

7. The method according to claim 1, further comprising forming red- to black-brown pigmented emersed culture portions, which are produced on a mineral salt-glucose-agar containing another ammonium salt as sole nitrogen source, and selecting the red- to black-brown pigmented emersed culture portions for further processing.

8. The method according to claim 1, further comprising fermenting in the presence of a cation selected from the group consisting of zinc, iron and calcium.

9. The method according to claim 1, wherein the filter aid is gypsum.

10. The method according to claim 1, wherein the filter aid is calcite meal.

11. The method according to claim 1, further comprising swelling the filter cake, after the drying step e), with a swelling agent prior to the extraction step f).

12. The method according to claim 11, wherein the swelling agent is methanol.

13. The method according to claim 11, wherein the swelling agent is aqueous ammonia.

14. Method of fermentative production and isolation of Cyclosporin A by aerobic fermentation of a fungus microorganism in a medium containing a mineral salt and a nitrogen-containing substrate, comprising the steps of:
   a. using a producer strain selected from the group consisting of Wb 6-5 of *Tolypocladium inflatum*, IMET 43 899, *Sesquicilliopsis rosariensis* G.ARNOLD, IMET 43 888, *Sesquicilliopsis rosariensis* G.ARNOLD F605, IMET 43 887, mutants thereof and strains obtained therefrom by selection;
   b. culturing said producer strain in a culture medium containing an ammonium salt as a single source of nitrogen;
   c. after the culturing step b), mixing the culture medium with a filter aid to form a suspension;
   d. after said mixing step c), filtering the suspension to form a filter cake containing moist biomass and filter aid;
   e. extracting the filter cake with an extraction means to form an extract;
   f. purifying the extract to form a purified extract; and
   g. chromatographing the purified extract by preparative HPLC using a member selected from the group consisting of silica gel and aluminum oxide to obtain the cyclosporin A.

15. Method of fermentative production and isolation of Cyclosporin A by aerobic fermentation of a fungus microorganism in a medium containing a salt and a nitrogen-containing substrate, comprising the steps of:
   a. using a producer strain selected from the group consisting of Wb 6-5 of *Tolypocladium inflatum*, IMET 43 899, *Sesquicilliopsis rosariensis* G.AR-NOLD, IMET 43 888, *Sesquicilliopsis rosariensis* G.ARNOLD F605, IMET 43 887, mutants thereof and strains obtained therefrom by selection;

b. culturing said producer strain in a culture medium at temperatures from 20° to 30° C. for 5 to 11 days, said culture medium having an acidity of 3.0 to 7.5 containing an ammonium salt as a single source of nitrogen;

c. after the culturing step b), mixing the culture medium with a filter aid to form a suspension;

d. after said mixing step c), filtering the suspension to form a filter cake;

e. extracting the filter cake with an extraction means to form an extract; and f. chromatographing the purified extract by preparative HPLC using a member selected from the group consisting of silica gel and aluminum oxide to obtain the cyclosporin A.

16. Method of fermentative production and isolation of Cyclosporin A by aerobic fermentation of a fungus microorganism in a medium containing a mineral salt and a nitrogen-containing substrate, comprising the steps of:

a. using a producer strain selected from the group consisting of Wb 6-5 of *Tolypocladium inflatum*, IMET 43 899, *Sesquicilliopsis rosariensis* G.AR-NOLD, IMET 43 888, *Sesquicilliopsis rosariensis* G.ARNOLD F605, IMET 43 887, mutants thereof and strains obtained therefrom by selection;

b. culturing said producer strain in a culture medium at temperatures from 20° to 30° C. for 5 to 11 days, said culture medium having an acidity of 3.0 to 7.5 and containing an ammonium salt as a single source of nitrogen;

c. after the culturing step b), mixing the culture medium with a filter aid to form a suspension;

d. after said mixing step c), filtering the suspension to form a filter cake;

e. extracting the filter cake with an extraction means to form an extract; and f. chromatographing the purified extract by preparative HPLC using a member selected from the group consisting of silica gel and aluminum oxide to obtain the cyclosporin A.

* * * * *